(12) United States Patent
Kriesel

(10) Patent No.: US 8,142,398 B1
(45) Date of Patent: Mar. 27, 2012

(54) FLUID DISPENSER

(75) Inventor: Marshall S. Kriesel, St. Paul, MN (US)

(73) Assignee: BioQuiddity, Inc., San Francisco, CA (US)

(*) Notice: Subject to any disclaimer, the term of this patent is extended or adjusted under 35 U.S.C. 154(b) by 0 days.

(21) Appl. No.: 12/925,076

(22) Filed: Oct. 12, 2010

(51) Int. Cl.
*A61M 5/00* (2006.01)

(52) U.S. Cl. ...................................................... 604/132

(58) Field of Classification Search .................. 604/131, 604/132, 134
See application file for complete search history.

(56) References Cited

U.S. PATENT DOCUMENTS

| | | | |
|---|---|---|---|
| 7,828,770 B2* | 11/2010 | Bivin et al. ................... | 604/132 |
| 2007/0156090 A1* | 7/2007 | Kriesel ......................... | 604/131 |
| 2007/0219501 A1* | 9/2007 | Kriesel et al. ................. | 604/185 |
| 2007/0219502 A1* | 9/2007 | Kriesel et al. ................. | 604/185 |
| 2008/0027376 A1* | 1/2008 | Kriesel et al. ................... | 604/84 |
| 2008/0027386 A1* | 1/2008 | Kriesel et al. ................. | 604/132 |
| 2008/0051701 A1* | 2/2008 | Kriesel ........................... | 604/82 |
| 2008/0228129 A1* | 9/2008 | Kriesel et al. ................... | 604/19 |
| 2008/0243077 A1* | 10/2008 | Bivin et al. ................... | 604/131 |
| 2008/0319385 A1* | 12/2008 | Kriesel et al. ................... | 604/88 |
| 2009/0024083 A1* | 1/2009 | Kriesel et al. ................... | 604/86 |
| 2009/0108511 A1* | 4/2009 | Bivin et al. ................... | 267/167 |
| 2009/0112149 A1* | 4/2009 | Kriesel et al. ................... | 604/19 |
| 2009/0112163 A1* | 4/2009 | Bivin et al. ................... | 604/132 |
| 2009/0254067 A1* | 10/2009 | Kriesel ........................ | 604/890.1 |
| 2009/0275888 A1* | 11/2009 | Kriesel et al. ................... | 604/86 |
| 2010/0056995 A1* | 3/2010 | Kriesel ............................ | 604/83 |
| 2010/0056996 A1* | 3/2010 | Kriesel ............................ | 604/85 |
| 2010/0056997 A1* | 3/2010 | Kriesel ............................ | 604/85 |
| 2010/0056998 A1* | 3/2010 | Kriesel et al. ................... | 604/85 |
| 2010/0094203 A1* | 4/2010 | Kriesel et al. ................... | 604/66 |
| 2010/0094218 A1* | 4/2010 | Kriesel et al. ................. | 604/132 |
| 2010/0094219 A1* | 4/2010 | Kriesel et al. ................. | 604/134 |
| 2010/0222741 A1* | 9/2010 | Bivin et al. ................... | 604/132 |
| 2010/0241074 A1* | 9/2010 | Bivin et al. ................... | 604/132 |
| 2010/0312175 A1* | 12/2010 | Kriesel et al. ................... | 604/30 |
| 2010/0312187 A1* | 12/2010 | Kriesel et al. ................. | 604/132 |
| 2011/0077593 A1* | 3/2011 | Kriesel et al. ................. | 604/134 |
| 2011/0077594 A1* | 3/2011 | Kriesel et al. ................. | 604/134 |
| 2011/0082422 A1* | 4/2011 | Joshi et al. ................... | 604/113 |
| 2011/0092904 A1* | 4/2011 | Kriesel et al. ................. | 604/131 |
| 2011/0098645 A1* | 4/2011 | Kriesel et al. ................. | 604/132 |
| 2011/0251556 A1* | 10/2011 | Kriesel et al. ................. | 604/132 |

* cited by examiner

*Primary Examiner* — Nicholas Lucchesi
*Assistant Examiner* — Aarti B Berdichevsky
(74) *Attorney, Agent, or Firm* — James E. Brunton

(57) ABSTRACT

A dispensing device for dispensing pain management medicaments to a patient comprising first and second threadably interconnectable sub-assemblies. The first of these sub-assemblies houses a novel collapsible fluid reservoir defining component while the second comprises a fluid delivery and control assembly that includes a novel flow control means that functions to control the flow of medicinal fluid from the fluid reservoir of the collapsible reservoir defining component toward the patient via a plurality of fluid flow control passageways.

20 Claims, 16 Drawing Sheets

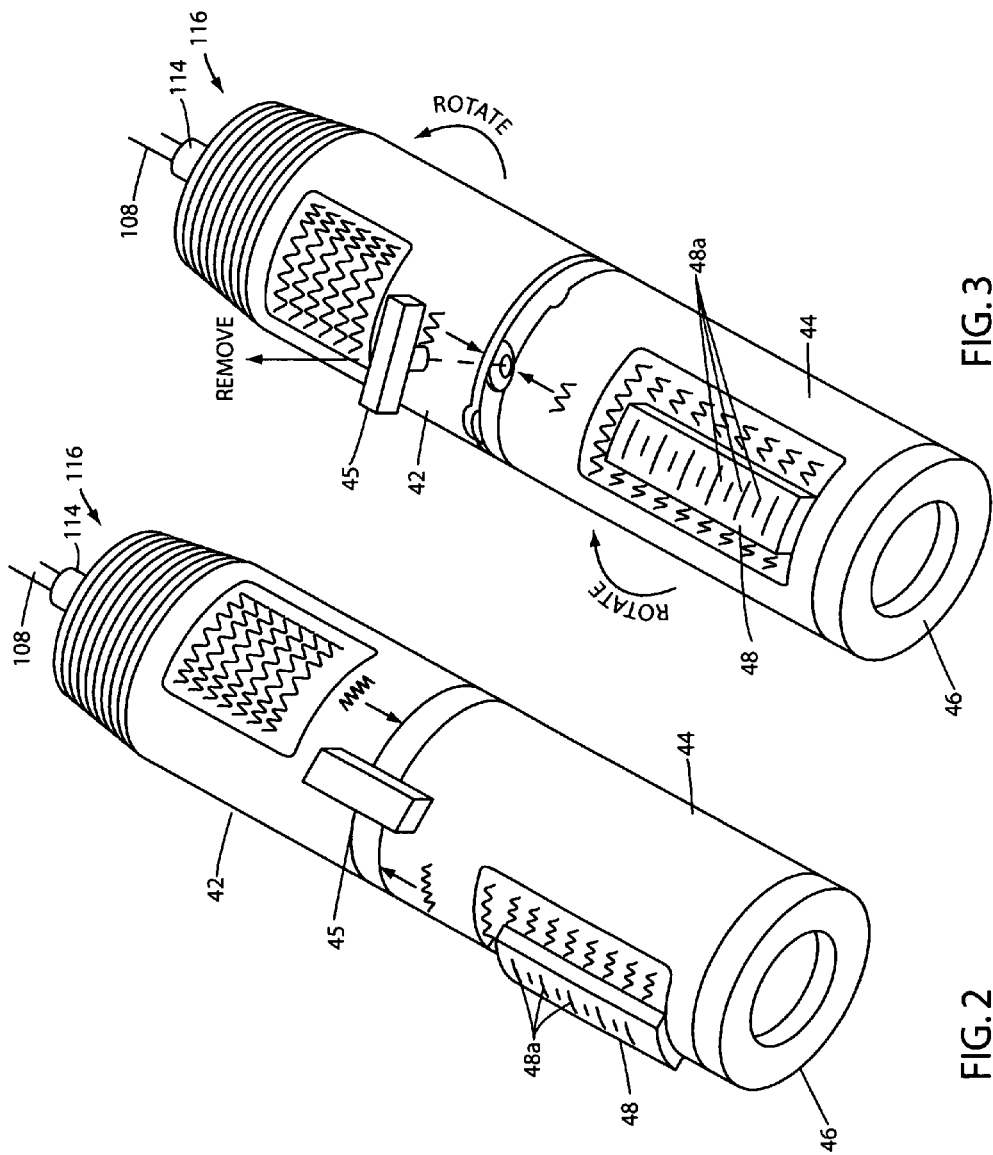

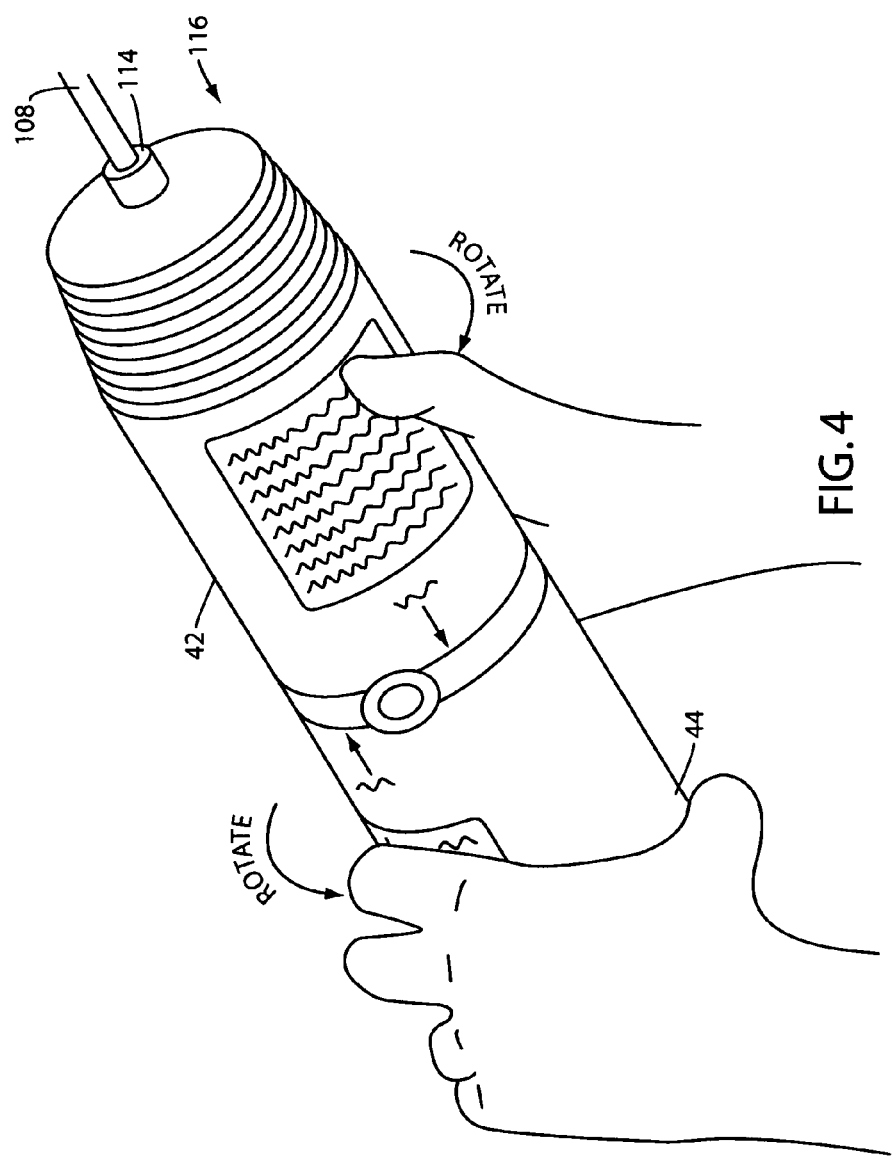

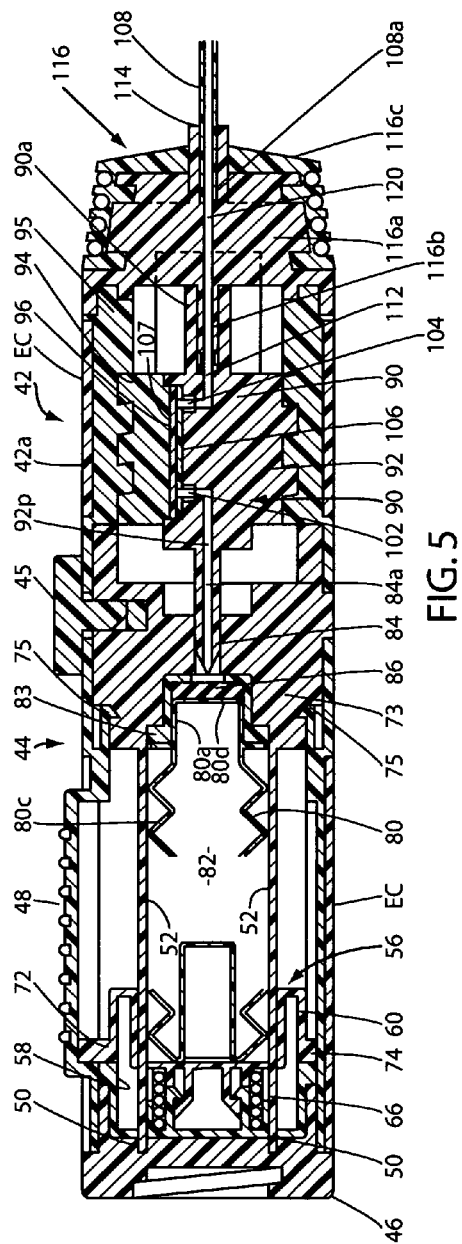
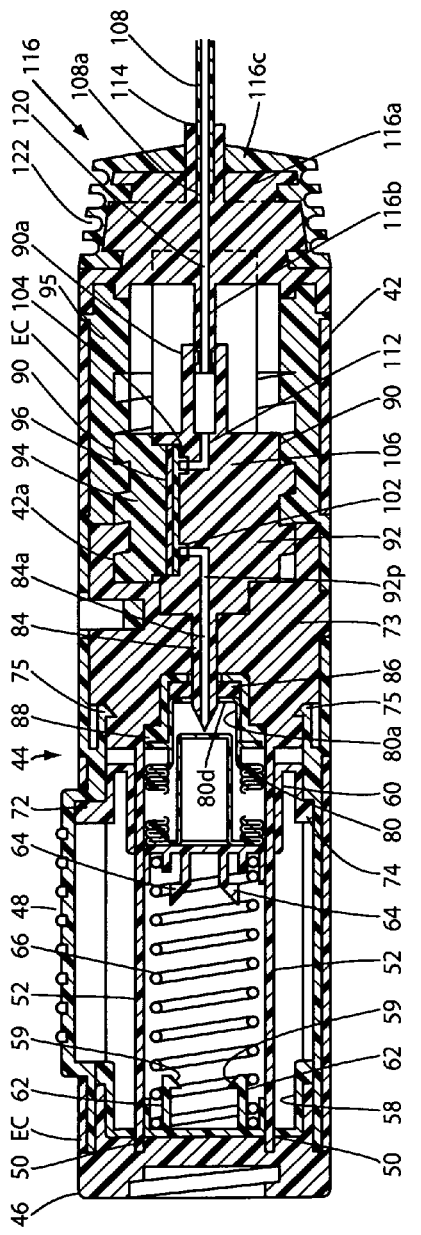

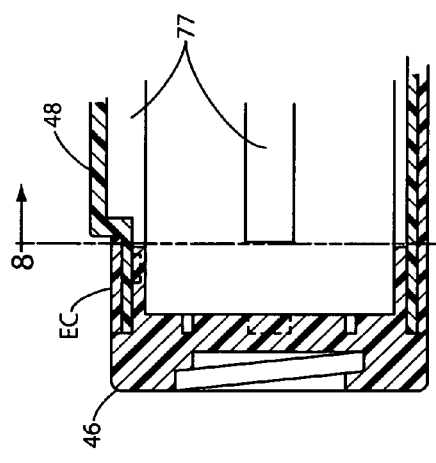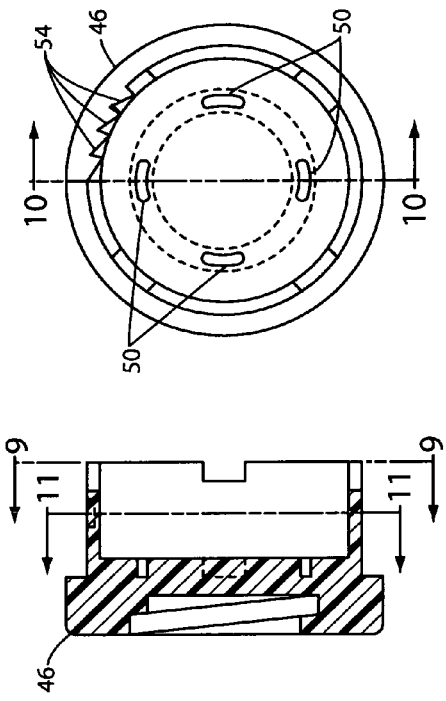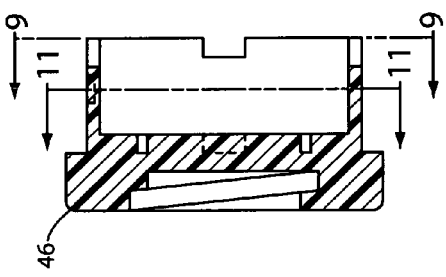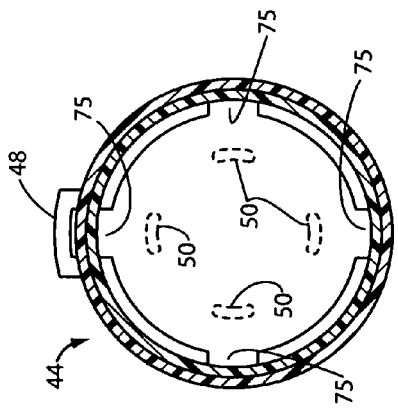

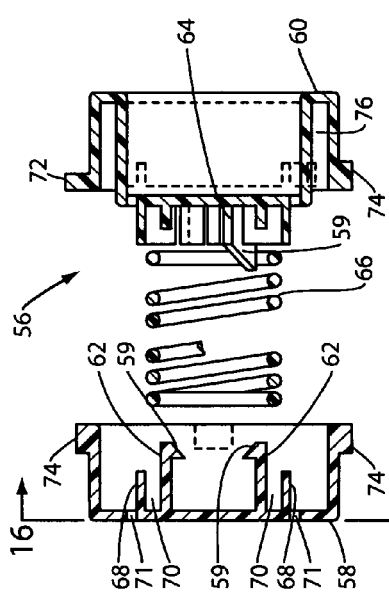
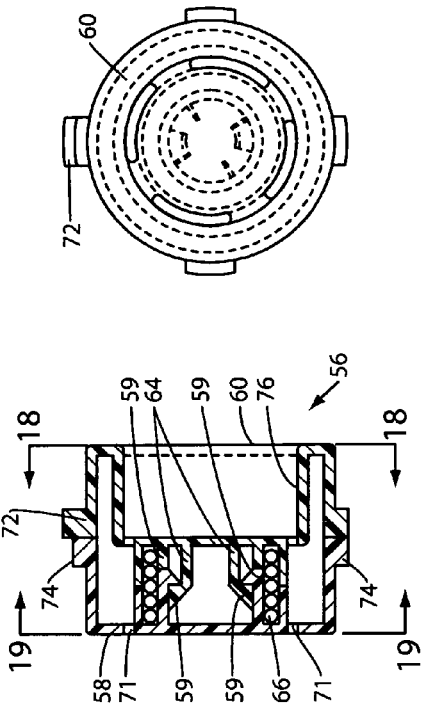
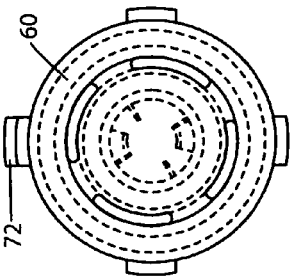
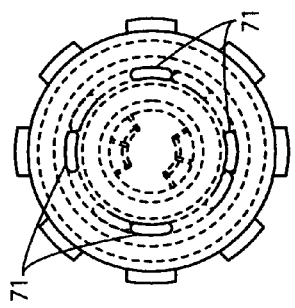
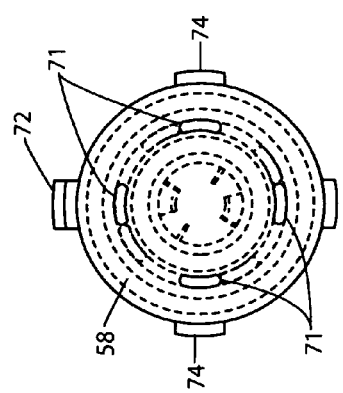
FIG. 15
FIG. 17
FIG. 18
FIG. 16
FIG. 19

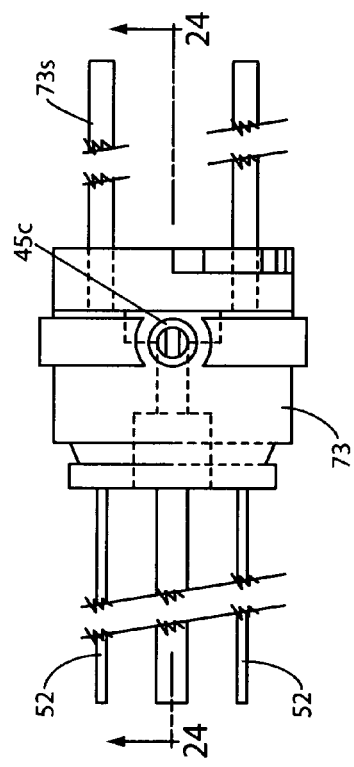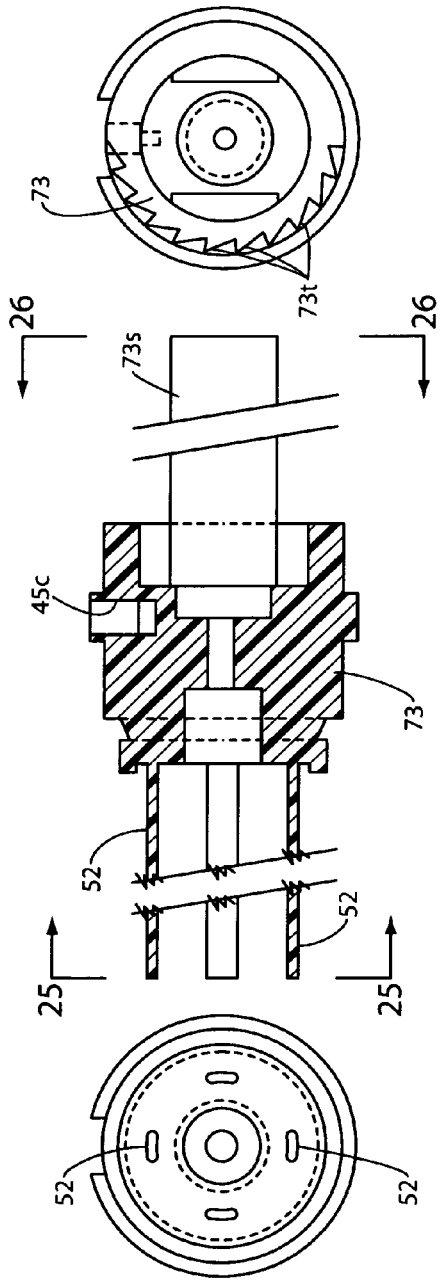

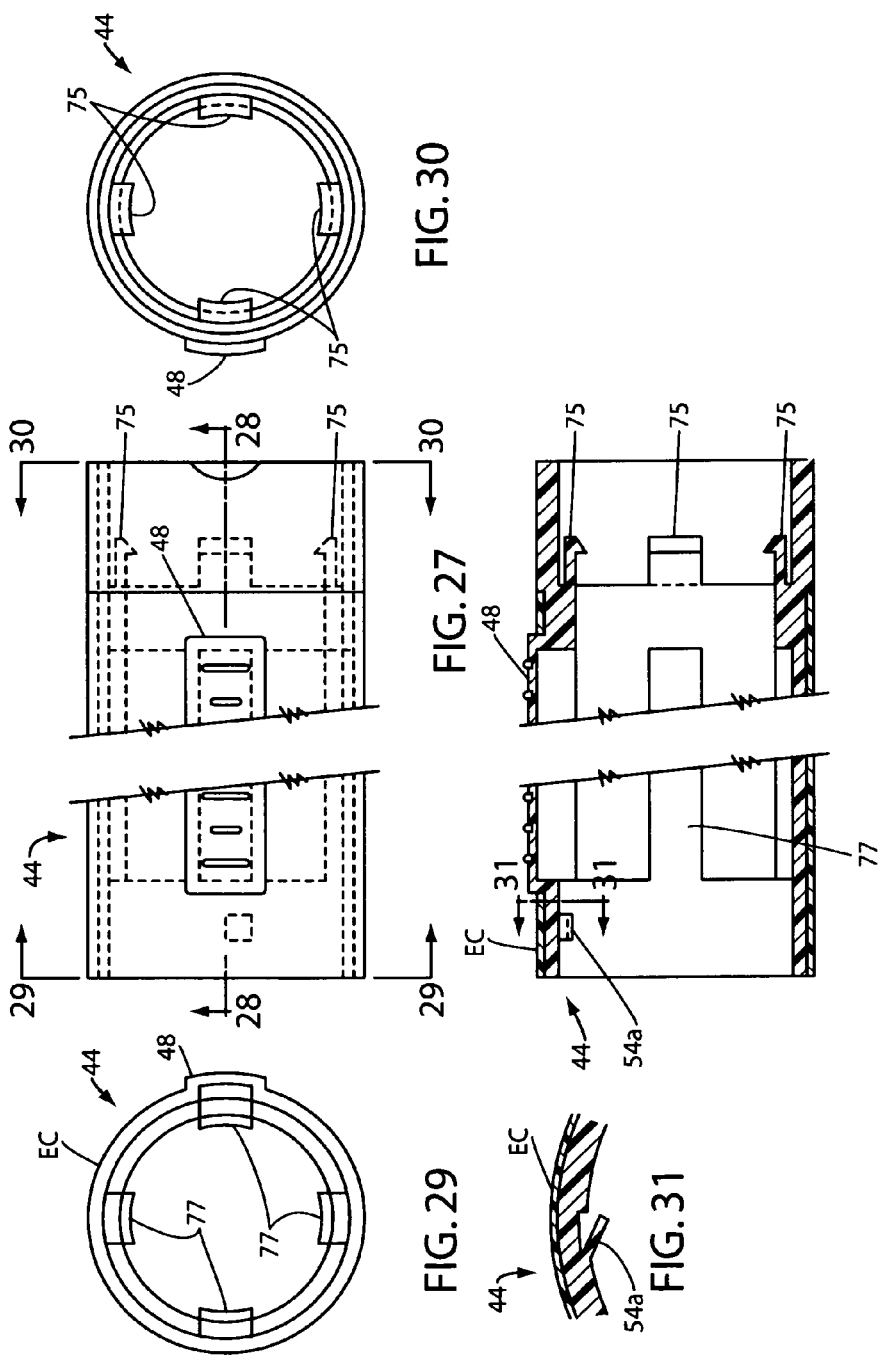

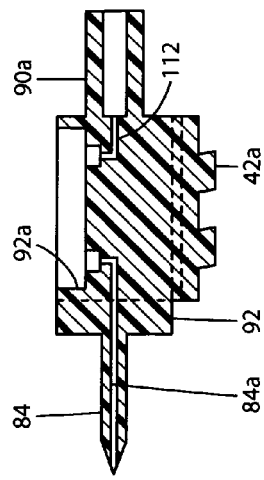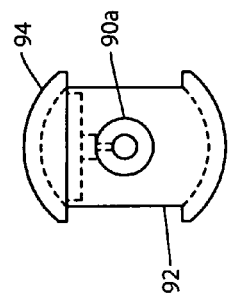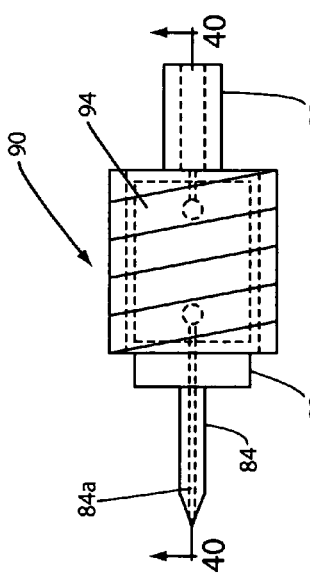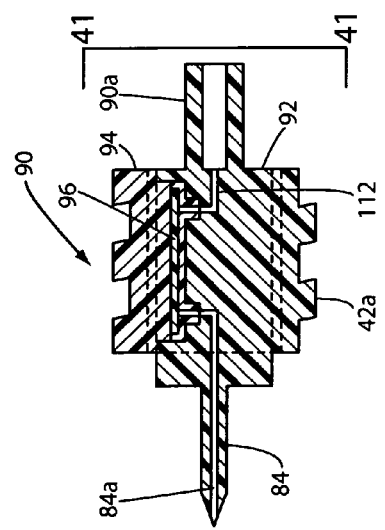
FIG. 39
FIG. 40
FIG. 41
FIG. 42

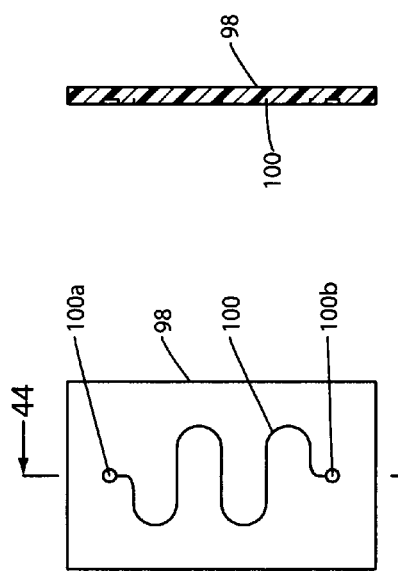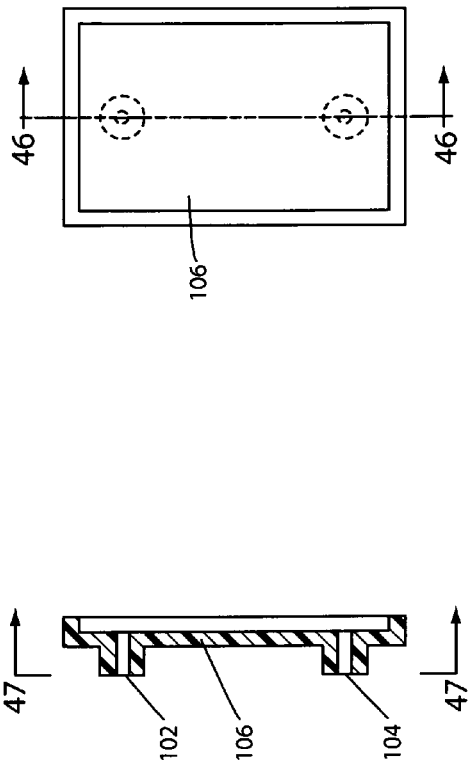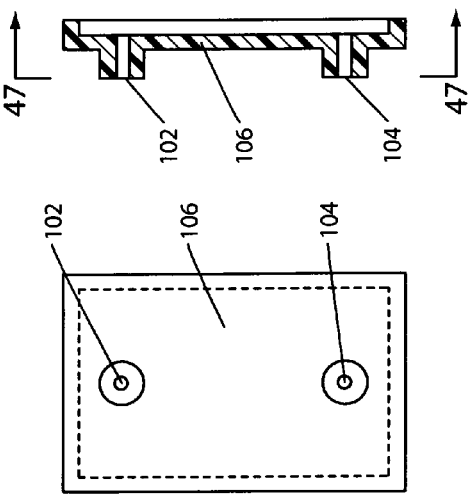

FLUID DISPENSER

CROSS-REFERENCE TO RELATED APPLICATIONS

Not applicable

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not applicable

BACKGROUND OF THE INVENTION

1. Field of the Invention

The present invention relates generally to fluid dispensing devices. More particularly, the invention concerns a novel dispenser for dispensing medicinal fluids, such as Bupivacane to ambulatory patients that uniquely comprises a flow rate control system that regulates the pressure of medicaments flowing to the patient.

2. Description of Related Art Including Information Disclosed Under 37 CFR 1.97 and 1.98

A number of different types of medicament dispensers for dispensing medicaments to ambulatory patients have been suggested in the past. Many of the devices seek either to improve or to replace the traditional gravity flow and hypodermic syringe methods which have been the standard for delivery of liquid medicaments for many years.

With regard to the prior art, one of the most versatile and unique fluid delivery apparatus developed in recent years is that developed by one of the present inventors and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly.

Another prior art patent issued to one of the present applicants, namely U.S. Pat. No. 5,743,879, discloses an injectable medicament dispenser for use in controllably dispensing fluid medicaments such as insulin, anti-infectives, analgesics, oncolylotics, cardiac drugs, bio-pharmaceuticals, and the like from a pre-filled container at a uniform rate. The dispenser, which is quite dissimilar in construction and operation from that of the present invention, includes a stored energy source in the form of a compressively deformable, polymeric, elastomeric member that provides the force necessary to controllably discharge the medicament from a pre-filled container which is housed within the body of the device. After having been deformed, the polymeric, elastomeric member will return to its starting configuration in a highly predictable manner.

A more recent fluid dispensing apparatus invented by one of the named inventors of the present application is disclosed in U.S. Pat. No. 7,220,245. This apparatus comprises a compact fluid dispenser for use in controllably dispensing fluid medicaments, such as antibiotics, oncolylotics, hormones, steroids, blood clotting agents, analgesics, and like medicinal agents from prefilled containers at a uniform rate. The dispenser uniquely includes a stored energy source that is provided in the form of a substantially constant-force, compressible-expandable wave spring that provides the force necessary to continuously and uniformly expel fluid from the device reservoir. The device further includes a fluid flow control assembly that precisely controls the flow of medicament solution to the patient.

BRIEF SUMMARY OF THE INVENTION

By way of brief summary, one form of the dispensing device of the present invention for dispensing pain management medicaments to a patient comprises first and second threadably interconnectable sub-assemblies. The first of these sub-assemblies houses a fluid reservoir defining component while the second comprises a fluid delivery and control assembly that includes a novel flow control means that functions to control the flow of medicinal fluid from the fluid reservoir of the first sub-assembly toward the patient via a plurality of fluid flow control passageways.

By way of brief background, the fluid dispensing system of the present invention has been created to provide safe and efficacious drug and fluid delivery in hospitals, surgery centers, home care, austere environments, and other alternate sites of care. The fluid delivery systems are uniquely configured for use at the point-of-care and will allow drug or fluid infusion to be initiated during virtually any phase of care, in any healthcare setting, and continue uninterrupted, while en-route to other medical facilities or during rehabilitation.

Additionally, the self-contained and therapy-specific nature of the fluid delivery systems functions to reduce the probability of costly and potentially life-threatening medication errors. In this regard, the fluid delivery systems of the invention are consistent with the growing trend of unit-dosing, where clinicians, pharmacists and regulators agree that a "unit of use" is the preferred form of containerization for liquid and solid medicines to be administered in hospital, home, or alternate site settings. Unit-dose packaging is preferred because of its inherent ability to reduce the possibility of medication error, while promoting the use of bar coding at the point of care. The unit-dose drug delivery dispensers of the present invention are also equally well suited for use in the inpatient hospital environment, where surgeries that are more complex, require longer recovery times, or cannot be sustained in a surgicenter setting, are still performed.

With the forgoing in mind, it is an object of the present invention to provide a novel safe and efficacious drug and fluid delivery system that can be efficiently used in hospitals, surgery centers, home care, austere environments, and other alternate sites of care.

Another object of the invention is to provide a drug and fluid delivery system of the aforementioned character that is specifically configured for use at the point-of-care and one which will allow drug or fluid infusion to be initiated during virtually any phase of care, in any healthcare setting, and continue uninterrupted, while en-route to other medical facilities or during rehabilitation.

Another object of the invention is to provide a fluid dispensing system that can be used for controllably dispensing at a uniform rate a wide variety of fluid medicaments, such as Bupivacane, Ropivaciane, Propofol and like medicinals.

Another object of the invention is to provide a pain management dispensing apparatus of the aforementioned character, of simple construction and one that can be used in the home care environment with a minimum amount of training.

Another object of the invention is to allow infusion therapy to be initiated quickly at the point of care without the assistance of a medical professional.

Another object of the invention is to provide a novel dispensing apparatus in which a stored energy source is provided in the form of a compressible, expandable or retractable member of novel construction that provides the force necessary to continuously and uniformly expel fluid from the device reservoir.

Another object of the invention is to provide a dispenser of the character described in the preceding paragraphs in which the stored energy source is provided in the form of a variable force spring that comprises a tightly coiled wound band of pre-hardened, perforated spring steel or stainless steel strip with built-in curvature so that each turn of the strip wraps tightly on its inner neighbor. When the strip is extended (deflected), the inherent stress resists the loading force the same as a common extension spring but at a variable rate.

Another object of the invention is to provide a dispenser of the class described which includes a fluid flow control assembly that precisely controls the flow of the medicament solution to the patient.

Another object of the invention is to provide a fluid dispensing apparatus that enables precise variable flow rate selection.

Another object of the invention is to provide a fluid dispensing apparatus of the character described in the preceding paragraphs that embodies an integrally formed, aseptically filled, unitary semi-rigid collapsible container that includes a fluid reservoir that contains the beneficial agents to be delivered to the patient.

Another object of the invention is to provide a fluid dispensing apparatus of the class described which is compact and lightweight, is easy for ambulatory patients to use, and is extremely reliable in operation.

Another object of the invention is to provide a fluid dispensing apparatus that is easy and inexpensive to manufacture in large quantities.

BRIEF DESCRIPTION OF SEVERAL VIEWS OF THE DRAWINGS

FIG. 2 is a generally perspective view of the body portion of the form of the fluid dispensing system shown in FIG. 1.

FIG. 3 is a generally perspective view similar to FIG. 2, but illustrating the manner of operation of the device to enable initiation of fluid flow toward the patient.

FIG. 4 is a generally perspective view similar to FIG. 3, illustrating the manner of operation of the device to initiate fluid flow toward the patient.

FIG. 5 is a longitudinal cross-sectional view of the body portion of the fluid dispensing system shown in FIG. 2 of the drawings.

FIG. 6 is a longitudinal cross-sectional view of the body portion of the fluid dispensing system similar to that shown in FIG. 5 of the drawings, but illustrating the position of the various components of the device following the fluid delivery step.

FIG. 7 is a fragmentary, longitudinal cross-sectional view similar to FIG. 2, but showing only the configuration of the base portion of the device.

FIG. 8 is a cross-sectional view taken along lines 8-8 of FIG. 7.

FIG. 9 is a view taken along lines 9-9 of FIG. 10.

FIG. 10 is a cross-sectional view taken along lines 10-10 of FIG. 9.

FIG. 11 is a cross-sectional view taken along lines 11-11 of FIG. 10.

FIG. 15 is a cross-sectional, exploded view of the plunger housing shown in FIG. 14.

FIG. 16 is a view taken along lines 16-16 of FIG. 15.

FIG. 17 is a cross-sectional view of the plunger housing of FIG. 15 shown in an assembled configuration.

FIG. 18 is a view taken along lines 18-18 of FIG. 17.

FIG. 19 is a view taken along lines 19-19 of FIG. 17.

FIG. 23 is a top plan view of the main dispenser substrate of the apparatus of the invention shown in the central portion of FIG. 5 of the drawings.

FIG. 24 is a cross-sectional view taken along lines 24-24 of FIG. 23.

FIG. 25 is a view taken along lines 25-25 of FIG. 24.

FIG. 26 is a view taken along lines 26-26 of FIG. 24.

FIG. 27 is a top plan view of the rear housing of the apparatus as shown in the rear portion of FIG. 1 and within which the reservoir plunger assembly and the collapsible container of the invention is mounted.

FIG. 28 is a cross-sectional view taken along lines 28-28 of FIG. 27.

FIG. 29 is a view taken along lines 29-29 of FIG. 27.

FIG. 30 is a view taken along lines 30-30 of FIG. 27.

FIG. 31 is a fragmentary cross-sectional view taken along lines 31-31 of FIG. 28.

FIG. 39 is a top plan view of the rate control assembly of the apparatus of the invention shown in FIG. 5.

FIG. 40 is a cross-sectional view taken along lines 40-40 of FIG. 39.

FIG. 41 is a view taken along lines 41-41 of FIG. 40.

FIG. 42 is a cross-sectional view of the rate control base of the rate control assembly shown in FIG. 39.

FIG. 43 is a top plan view of one form of the rate control plate of the rate control means of the apparatus of the invention.

FIG. 44 is a view taken along lines 44-44 of FIG. 43.

FIG. 45 is a top plan view of the rate control plate housing of the rate control means of the apparatus of the invention.

FIG. 46 is a cross-sectional view taken along lines 46-46 of FIG. 45.

FIG. 47 is a view taken along lines 47-47 of FIG. 46.

DETAILED DESCRIPTION OF THE INVENTION

Definitions

As Used Herein the Following Terms Mean

Unitary Container:

A closed container formed from a single component.

Continuous/Uninterrupted Wall:

A wall having no break in uniformity or continuity.

Hermetically Sealed Container:

A container that is designed and intended to be secure against the entry of microorganisms and to maintain the safety and quality of its contents after pressurizing.

Aseptic Processing:

The term 'aseptic processing' as it is applied in the pharmaceutical industry refers to the assembly of sterilized components and product in a specialized clean environment.

Sterile Product:

A sterile product is one that is free from all living organisms, whether in a vegetative or spore state.

Blow-Fill-Seal Process:

The concept of aseptic blow-fill-seal (BFS) is that a container is formed, filled, and sealed as a unitary container in a continuous manner without human intervention in a sterile enclosed area inside a machine. The process is multi-stepped; pharmaceutical grade resin is extruded into a tube, which is then formed into a container. A mandrel is inserted into the newly formed container and filled. The container is then sealed, all inside a sterile shrouded chamber. The product is then discharged to a non-sterile area for packaging and distribution.

Collapsible Container:

A dispensing apparatus in which one or more walls of the container are made of a material which will deform (collapse) when pressure is applied thereto; or a dispensing apparatus having a collapsible or telescoping wall structure.

Figure 1:
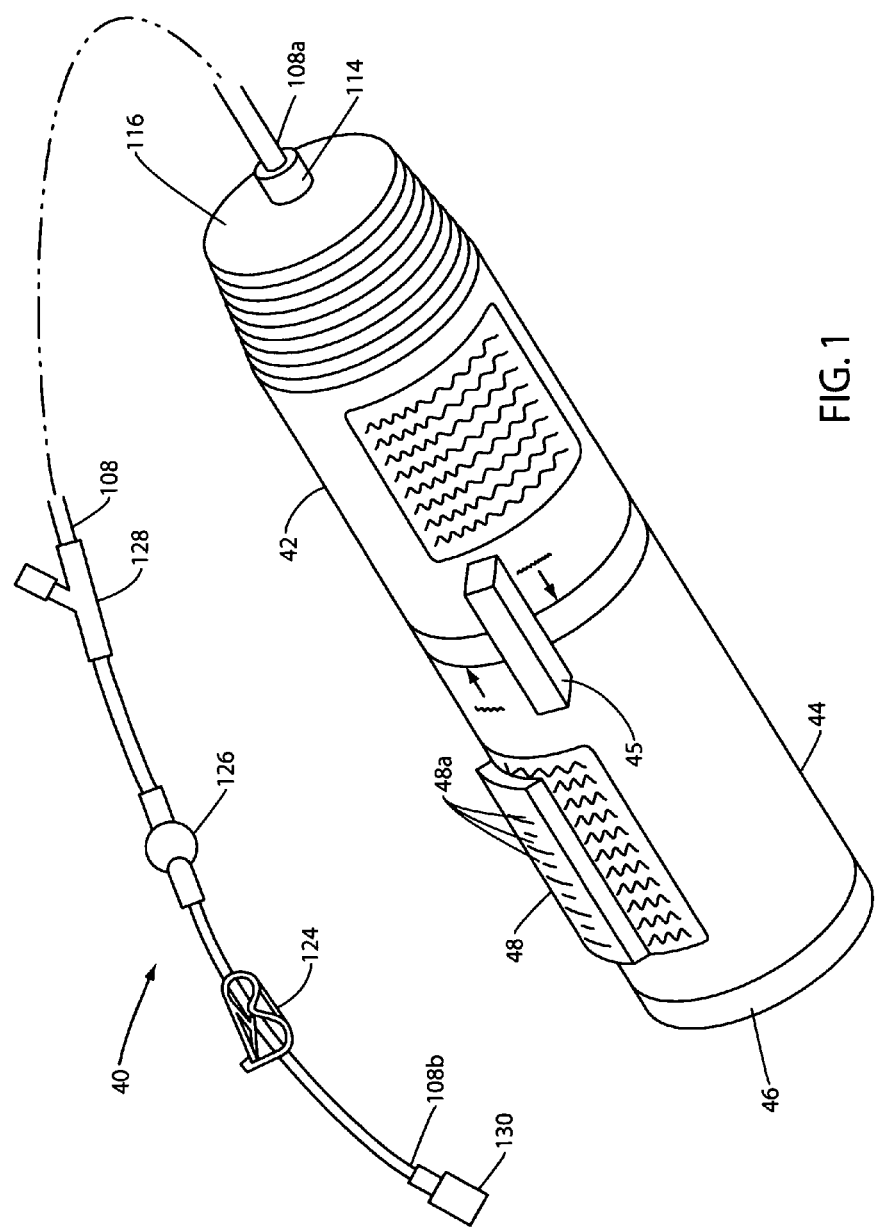
FIG. 1 is a generally perspective view of one form of the fluid dispensing system of the present invention.
Figures 12, 13, 14:
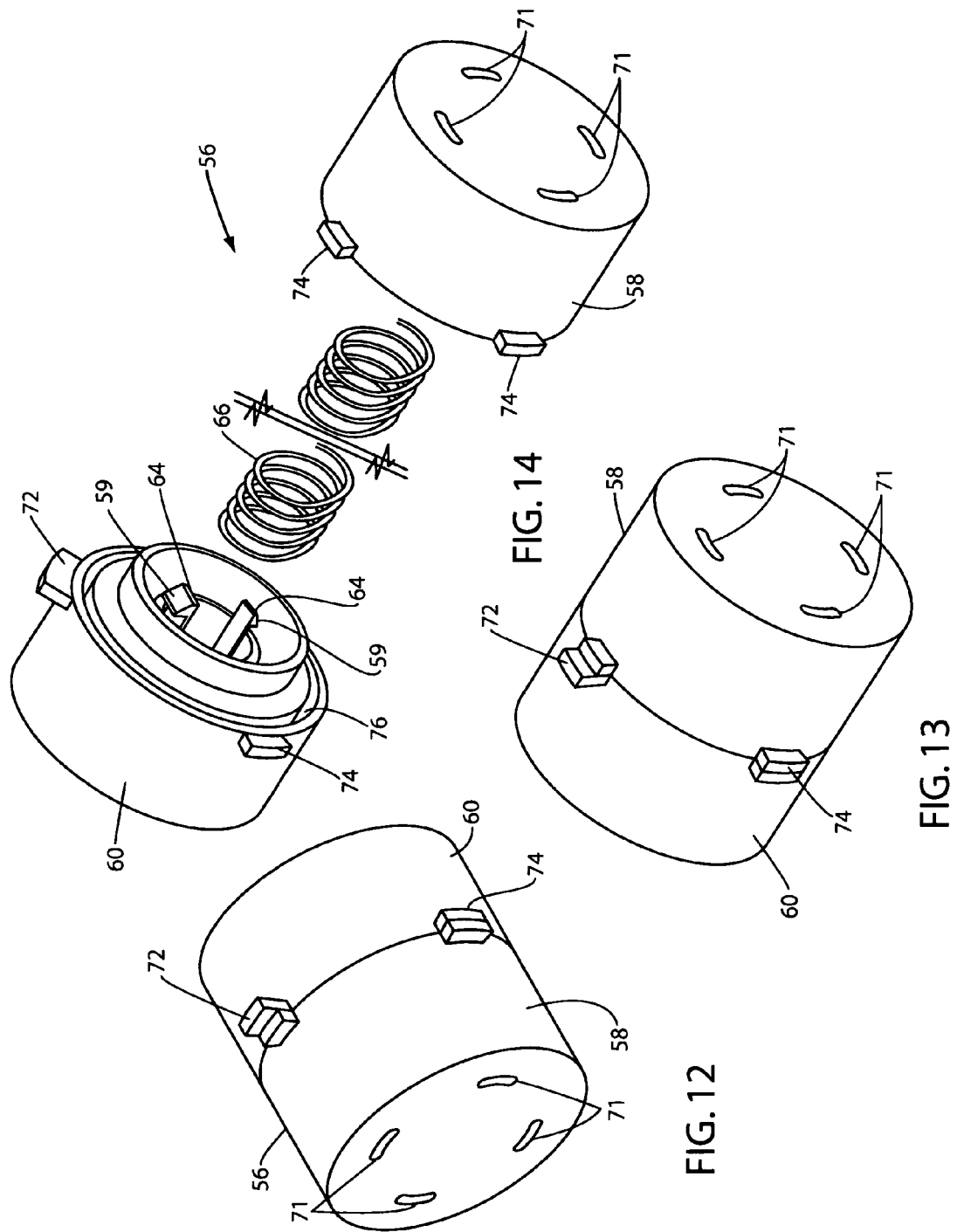
FIG. 12 is a generally perspective rear view of the plunger housing of the device that is mounted within the rear housing of the device shown in the left-hand portion FIG. 1.
FIG. 13 is a generally perspective front view of the plunger housing.
FIG. 14 is a generally perspective exploded view of the plunger housing shown in FIG. 13.

Referring to the drawings and particularly to FIGS. 1 through 5, one form of the fluid dispensing apparatus of the present invention for dispensing medicaments to a patient is there shown and generally designated in FIG. 1 by the numeral 40. As indicated in FIG. 4, the fluid dispensing apparatus here comprises a front or first housing 42 and a rear, or second housing 44 that is connected to the first housing. As will be described in greater detail hereinafter, when the apparatus is in the configuration shown in FIG. 1, no fluid can flow toward the patient. However, upon operation of the rotatable housing lock 45 of the apparatus, rotation of the front and rear housings relative to one another from a first position to a second position can be accomplished in the manner indicated in FIG. 4 of the drawings thereby rendering the device operable so as to permit fluid flow toward the patient.

Interconnected with and closing the rear portion of rear housing 44 is an internally threaded dispenser base 46. Formed in the upper surface of rear housing 44 is an indicator window 48, the purpose of which will presently be described (see also FIG. 8). Base 46 is provided with a plurality of circumferentially spaced apart cavities 50 that locate and support four circumferentially spaced container guides 52 that function to position the collapsible container of the invention within the rear housing and to guide its forward travel in the manner illustrated in FIG. 5 of the drawings. As illustrated in FIGS. 9 and 11, base 46 is also provided with a plurality of anti-rotational teeth 54 that function to prevent rotation of the dispenser base relative to the rear housing 44.

Disposed internally of the rear housing is the important plunger assembly 56, the character of which is illustrated in FIGS. 12 through 18 of the drawings. Plunger assembly 56 comprises a rear or first plunger housing 58 and a front or second plunger housing 60 that is interconnected with the rear housing 58 by mating locking tabs. More particularly, rear plunger housing 58 is provided with a plurality of circumferentially spaced, forwardly extending locking tabs 62, while front plunger housing 60 is provided with a plurality of circumferentially spaced, rearwardly the extending locking tabs 64. When the front and rear plunger housings are interconnected in the manner shown in FIG. 17 of the drawings, the teeth-like end portions 59 of the locking tabs are in locking engagement. However, upon relative rotation of the front and rear housings in a manner presently to be described, the teeth-like end portions of the locking tabs will move out of engagement with one another thereby permitting a spring 66, which is housed within rear housing 58, to urge the front plunger housing 60 forwardly in the manner illustrated in FIG. 15 from a first position to a second position. As best seen by referring to FIG. 15, locking tabs 62 cooperate with inwardly extending projections 68, which are formed on the interior of rear plunger housing 58, to form a spring locating and receiving channel 70 that locates and receives the rearward extremity of spring 66 (see FIG. 17). Rear plunger housing 58 is also provided with a plurality of circumferentially spaced apart openings 71 that receive the previously mentioned container guides 52 that form a part of the important main dispenser substrate 73 of the invention (FIGS. 23 and 24). As best seen in FIGS. 5 and 6 of the drawings, housing 44 is interconnected with the main dispenser substrate 73 by means of circumferentially spaced apart housing locking tabs 75.

Front plunger housing 60 is provided with an outwardly extending fluid indicator tab 72, the purpose of which will presently be described, and a plurality of guide tabs 74 (FIGS. 12, 13, 14) that are received within a plurality of circumferentially spaced apart guide grooves 75 formed in housing 44 (FIG. 7) and function to guide forward travel of the forward plunger housing 60 within rear housing 44. Front plunger housing 60 is also provided with a generally cylindrically shaped cavity 76 (FIG. 14) that receives the reservoir guides 52.

Figure 20:
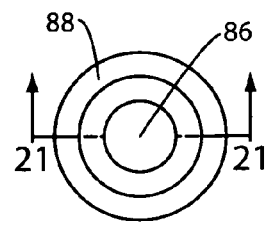
FIG. 20 is a top plan view of one form of the hermetically sealed collapsible container of the invention that is mounted within the rear housing of the device.
Figure 22:
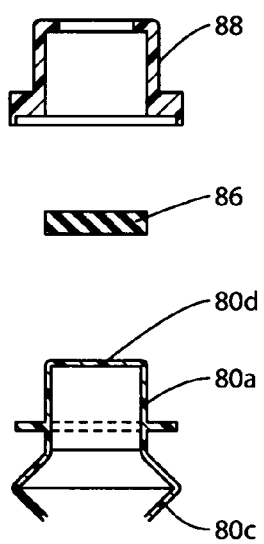
FIG. 22 is an enlarged, fragmentary exploded view of the upper portion of the collapsible container shown in FIG. 21.
Figure 21:
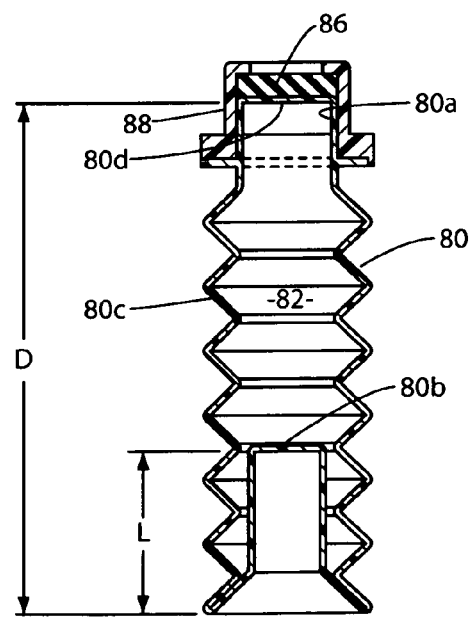
FIG. 21 is a cross-sectional view taken along lines 21-21 of FIG. 20.
Figure 32:
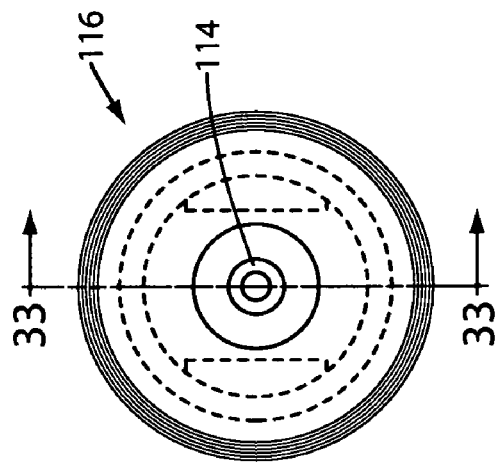
FIG. 32 is a front view of the front housing of the apparatus of the invention shown in the right-hand portion of FIG. 1 and within which said rate control means of the invention is mounted.

As previously mentioned, received within the circumferentially spaced reservoir guides 52 is the important hermetically sealed collapsible container, or fluid reservoir defining component 80. As best seen in FIGS. 20, 21 and 22, container 80 includes a front neck portion 80*a*, a rear, inwardly extending, ullage defining wall portion 80*b* and a collapsible accordion-like, continuous, uninterrupted side wall 80*c* that interconnects the front and rear portion of the container and cooperates therewith to define a fluid reservoir 82. As illustrated in FIG. 21, ullage defining wall portion 80b has a length "L" that is approximately ⅓ the depth "D" of the fluid reservoir 82. In a manner presently to be described, fluid medicament reservoir 82 is accessible via a piercing member 84 (FIGS. 5 and 6) which forms the inlet to the fluid delivery and control assembly of the invention, the character of which will presently be described. More particularly, piercing member 84 is adapted to pierce a top, or closure wall 80d of the collapsible container 80 as well as a pierceable septum 86 (FIGS. 21 and 22) which is secured in position over closure wall 80d by means of a closure cap 88, which is affixed to the neck portion 80a of the reservoir defining component.

The reservoir defining component, or collapsible container 80, is uniquely formed using an aseptic blow fill technique and the reservoir portion of the container is sealed by the thin closure or top wall 80d. The continuous top, bottom and accordion side walls cooperate to define the sealed medicament reservoir 82. Prior to heat sterilization of the container, the piercable septum 86 is positioned over the closure wall and the closure cap 88 is positioned over the piercable septum and is secured to the neck portion 80a by any suitable means such as adhesive bonding, sonic welding or heat welding. The container 80 is held in position within housing 44 by the front plunger housing 60, the dispenser substrate 73 and the circumferentially spaced reservoir guides 52.

Figure 35:
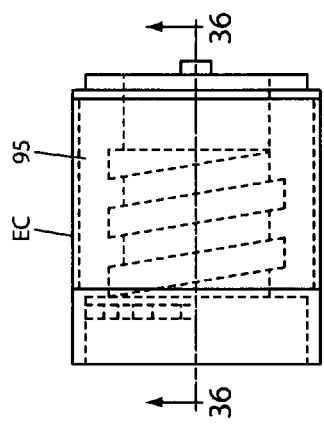
FIG. 35 is a top plan view of the internally threaded housing portion of the apparatus disposed immediately rearwardly of the housing assembly shown in FIG. 33.
Figure 36:
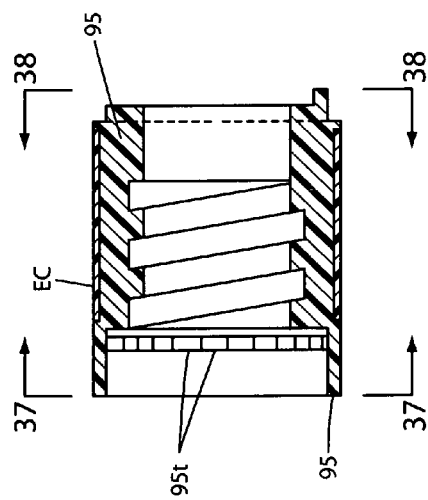
FIG. 36 is a cross-sectional view taken along lines 36-36 of FIG. 35.
Figure 37:
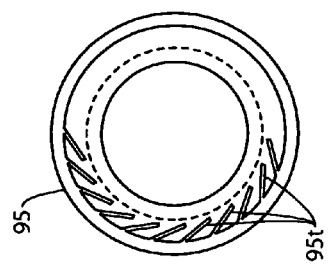
FIG. 37 is a view taken along lines 37-37 of FIG. 36.

Piercing member 84 forms a part of and provides the inlet to the fluid delivery and control assembly 90 of the invention that is housed within housing 42. In addition to piercing member 84, fluid delivery and control assembly 90 includes an externally threaded rate control base 92 (FIGS. 39, 40 and 42) and an externally threaded rate control cover 94 (FIGS. 39, 40) that is interconnected with rate control base 92. Rate control base 92 is provided with a rate control cavity 92a (FIG. 42) that houses the novel fluid flow rate control assembly 96 that functions to control the rate of flow of medicinal fluid toward the patient. As depicted in FIG. 5 of the drawings, rate control assembly 90 is threadably interconnected through an internally threaded sleeve 95 (FIGS. 35 and 36) carried within housing 42 and upon relative rotation of housings 42 and 44, is movable from the retracted position shown in FIG. 5 to the advanced position shown in FIG. 6.

As best seen in FIGS. 43 through 47, fluid flow rate control assembly 96 comprises a generally planar shaped rate control plate 98, which as shown in FIG. 43 is provided with a serpentine micro-channel 100 having an inlet 100a and an outlet 100b. Micro channel 100 which is controllably etched into rate control plate 98, communicates with an inlet port 102 and with an outlet port 104 formed in rate control cover plate 106 (FIGS. 46 and 47). Cover plate 106 cooperates with rate control plate 98 to define a fluid passageway 107 (FIG. 5), the length, width and depth of which determines the rate at which the fluid will flow from inlet port 102 toward outlet port 104.

Figure 33:
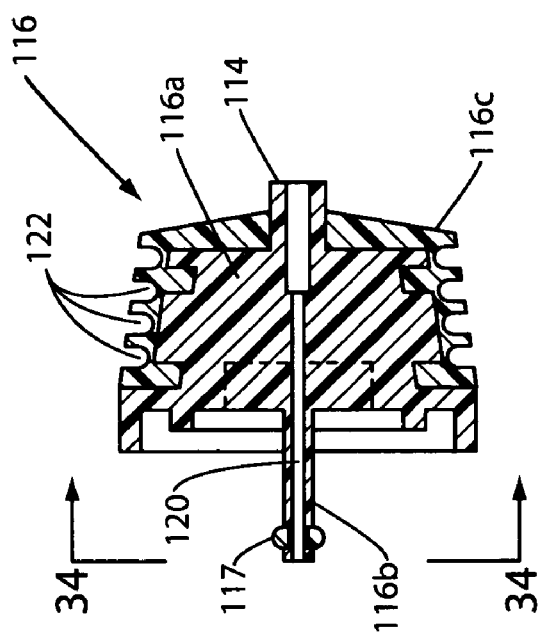
FIG. 33 is a cross-sectional view taken along lines 33-33 of FIG. 32.
Figure 34:
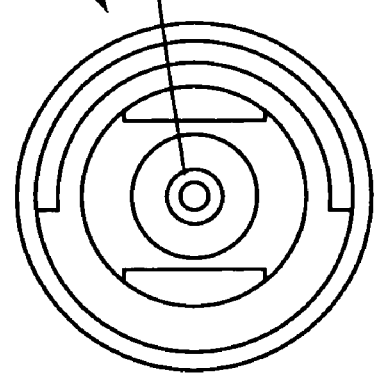
FIG. 34 is a view taken along lines 34-34 of FIG. 33.
Figure 38:
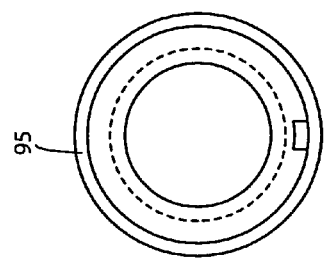
FIG. 38 is a view taken along lines 38-38 of FIG. 36.

As shown in FIGS. 5 and 6 of the drawings, inlet port 102 communicates with the internal passageway 84a of penetrating member 84 via a passageway 107 formed in rate control base 92. Outlet port 104 communicates with the administration line 108 of a conventional administration set 110 via a passageway 112 formed in rate control base 92. Administration line 108 is sealably interconnected with an outlet port 114 formed on the front housing assembly 116 of the invention which is connected to sleeve 95 carried in front housing 42 in the manner illustrated in FIG. 5 of the drawings. Front housing assembly 116 comprises a body portion 116a having a rearwardly extending tubular portion 116b that is telescopically receivable within a forwardly extending tubular extension 90a formed on the fluid delivery and control assembly 90 (FIGS. 40 and 42). A conventional O-ring 117 (FIG. 33) is carried by rearwardly extending tubular portion 116b and functions to prevent fluid leakage between the tubular portion 116b and the tubular extension 90a. With the construction thus described, the proximal end 108a of the administration line is in communication via passageway 112 with an outlet fluid passageway 120 formed in front housing assembly 116.

Body portion 116a of front housing assembly 116 is covered by a co-molded elastomer 116c within which a plurality of administration line-receiving grooves 122 are formed. During transport and storage of the dispensing device of the invention, the administration line can be conveniently coiled about the front housing assembly 116 so that it resides within the administration line receiving grooves 122.

As illustrated in FIG. 1 of the drawings, disposed between the proximal end 108a and the distal end 108b of the administration line are a conventional clamp 124, a conventional gas vent and filter 126, and a generally Y-shaped injector site, generally designated by the numeral 128. A luer connector 130 of conventional construction is provided at the distal end 108b of the administration line.

In using the apparatus of this latest form of the invention, the first step is to uncoil the administration line 108 from the front housing assembly so that the administration set is unfurled in the manner shown in FIG. 1 of the drawings. This done, the locking means of the invention is then operated. This novel locking means functions to prevent accidental relative rotation between the first and second assemblies 42 and 44. In the present form of the invention, the locking means comprises the previously identified rotatable housing lock 45 that extends into the main dispenser substrate 73 in the manner shown in FIG. 5 of the drawings. Rotation of the housing lock 45 and its removal from the main dispenser substrate in the manner illustrated in FIG. 6 of the drawings, permits relative rotation between housings 42 and 44.

Upon relative rotation of housings 42 and 44, fluid delivery and control assembly 90 will advance along the threads 42a provided on control assembly 90, into the position illustrated in FIG. 6 of the drawings. As control assembly 90 advances, penetrating member 84 will penetrate elastomeric member, or pierceable septum 86 and closure wall 80d of the collapsible container 80. Advance of control assembly 90 will also cause tubular portion 116b of front housing assembly 116 to telescope forwardly of extension 90a of control assembly 90 in the manner shown in FIG. 6 of the drawings.

Relative rotation of housings 42 and 44 will also cause the locking tabs 59 formed on rear plunger housing 58 and a front plunger housing 60 to disengage, thereby permitting spring 62 to urge the front plunger housing 60 to move forwardly of housing 44. As the front plunger housing moves forwardly, the collapsible container constrained between the advancing front plunger housing 60 and the dispenser substrate 73 will collapse in the manner illustrated in FIG. 6 of the drawings.

Communication between the fluid reservoir 82 and the internal passageway 84a of the penetrating member 84 having been established by the rearward movement of the fluid and delivery control assembly 90, the fluid contained within the fluid reservoir will be expelled from the reservoir 82 as a result of the forward movement of the front plunger housing 60, collapsing container wall 80c.

From the internal passageway 84a of penetrating member 84, the fluid will flow toward longitudinally extending fluid passageway 107 and then into inlet port 102 formed in rate control housing 106. Next, the fluid will flow into the inlet 100a of the serpentine micro-channel 100, through the micro channel 100 at a controlled rate, through the outlet 100b of the micro channel, into outlet port 104, into passageway 120 and finally into the administration set 40 for delivery to the patient at a precisely controlled rate, depending upon the configuration of the micro-channel 100.

In order that the caregiver can continuously monitor the amount of fluid remaining within the fluid reservoir 82, indicator means are provided for indicating the volume of fluid contained within the reservoir. In the present form of the invention, this indicator means comprises the previously identified fluid indicator tab 72 of front plunger housing 60 and the fluid indicator window 48 provided in housing 44 that enables the caregiver to view the fluid reservoir 82. Indicia 48a imprinted on the fluid indicator window (FIGS. 1 through 3) along with forward movement of the fluid indicator tab 72, provides an accurate indication of the volume of fluid contained within the reservoir.

Figure 51:
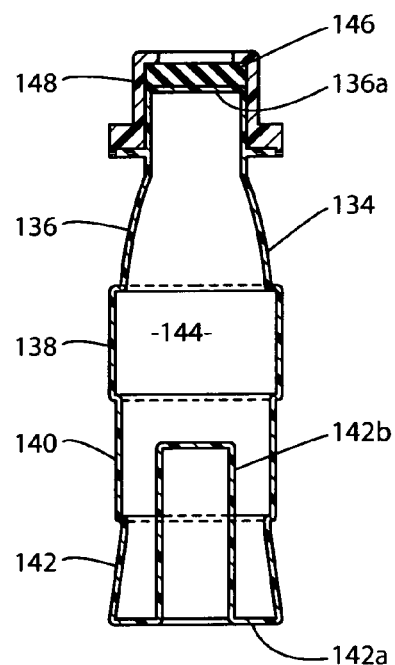
FIG. 51 is a cross-sectional view taken along lines 51-51 of FIG. 50.

Turning now to FIGS. 48 through 52, an alternate form of the apparatus of the invention is there shown. This form of the apparatus is similar in many respects to the embodiment illustrated in FIGS. 1 through 47 and like numerals are used in FIGS. 48 through 52 to identify like components. The primary difference between this alternate embodiment of the invention and the earlier described embodiments resides in the differently configured reservoir defining assembly 134. As best seen in FIG. 51, reservoir defining assembly 134 comprises telescoping portions 136, 138, 140 and 142 that cooperate to define a fluid medicament reservoir 144. More particularly, upper portion 136 is constructed and arranged so as to be telescopically received within intermediate portion 138. Similarly, portion 140 is constructed and arranged to be telescopically received within portion 138 and lower portion 142 is constructed and arranged to be telescopically received within intermediate portion 140 (see FIG. 49).

Upper portion 136 of the collapsible container 134 is sealed by a closure wall 136a, while lower portion 142 is closed by a bottom wall 142a that includes an inwardly extending ullage defining portion 142b. As in the earlier described embodiment of the invention, fluid medicament reservoir 144 is accessible via a penetrating member 84 which forms the inlet to the fluid delivery and control assembly of the invention, which is substantially identical in construction and operation to that previously described. More particularly, penetrating member 84 is adapted to pierce a top, or closure wall 136a of the collapsible container 134 as well as a pierceable septum 146 (FIGS. 51 and 52) which is secured in position over closure wall 136a by means of a closure cap 148 which is affixed to portion 136 of the reservoir defining component.

As in the earlier described embodiments of the invention, this latest apparatus comprises relatively rotatable front and rear housings 42 and 44 that are substantially identical in construction and operation to the housings previously described. Disposed internally of rear housing 44 is the important plunger housing 56, which is also substantially identical in construction to the previously described. As indicated in the drawings, penetrating member 84 is housed within housing 42. In addition to penetrating member 84, fluid delivery and control assembly 90 includes an externally threaded rate control base 92 (FIGS. 39, 40 and 42) and an externally threaded rate control cover 94 (FIG. 42) that is interconnected with rate control base 92. Rate control assembly 90 is also substantially identical in construction and operation to that previously described and includes the novel fluid flow rate control assembly 96 that functions to control the rate of flow of medicinal fluid toward the patient. As in the earlier described embodiment of the invention, rate control assembly 90 is threadably interconnected through sleeve 95 with housing 42 and upon relative rotation of housings 42 and 44, is movable from the retracted position shown in FIG. 48 to the advanced position shown in FIG. 49.

The fluid flow rate control assembly 96 of this latest form of the invention comprises a generally planar shaped rate control plate 98, which as shown in FIG. 43 is provided with a serpentine micro-channel 100 having an inlet 100a and an outlet 100b. Micro-channel 100 which is controllably etched into rate control plate 198, communicates with an inlet port 102 and with an outlet port 104 formed in a rate control housing 106 (FIGS. 46 and 47). The length, width and depth of the micro-channel determine the rate at which the fluid will flow from inlet port 102 toward outlet port 104.

Figure 49:
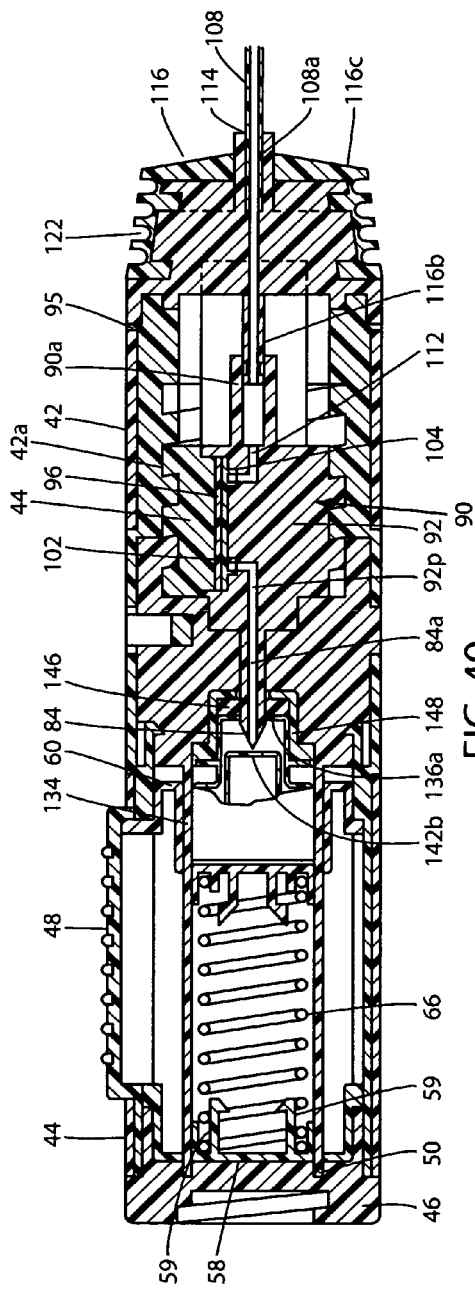
FIG. 49 is a longitudinal cross-sectional view of the body portion of the fluid dispensing system similar to that shown in FIG. 48 of the drawings, but illustrating the position of the various components of the device following the fluid delivery step.
Figure 48:
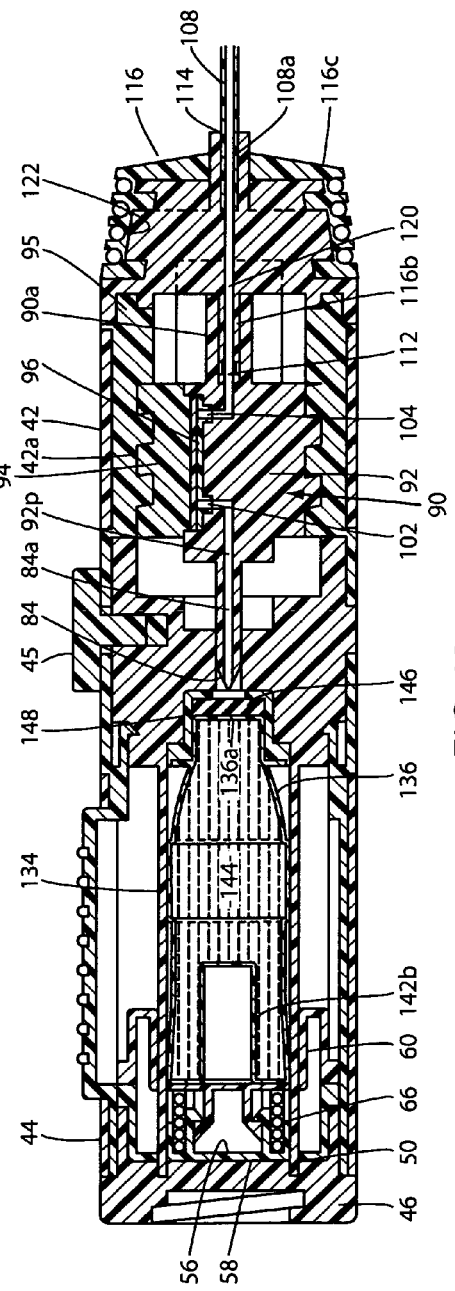
FIG. 48 is a longitudinal cross-sectional view of the body portion of an alternate form of the fluid dispensing system of the invention.
Figure 50:
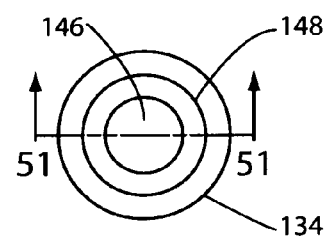
FIG. 50 is a top plan view of an alternate form of the hermetically sealed collapsible container of the invention that is mounted within the rear housing of the device illustrated in FIG. 48.
Figure 52:
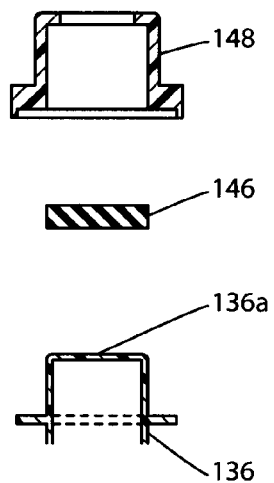
FIG. 52 is an enlarged, fragmentary exploded view of the upper portion of the collapsible container shown in FIG. 51.

As shown in FIGS. 48 and 49 of the drawings, inlet port 102 communicates with the internal passageway 84a of penetrating member 84 via passageway 107. Outlet port 104 communicates with the administration line 108 of a conventional administration set 110 via a passageway 112 formed in rate control base 92. Administration line 108 is sealably interconnected with an outlet port 114 formed on the front housing assembly 116 of the invention which is connected to housing 94 in the manner illustrated in FIG. 48 of the drawings.

In using the apparatus of this latest form of the invention, the first step is to uncoil the administration line 108 from the front housing assembly so that the administration set is unfurled in the manner shown in FIG. 1 of the drawings. This done, the locking means of the invention is then operated to permit relative rotation between housings 42 and 44.

Upon relative rotation of housings 42 and 44, fluid delivery and control assembly 90 will advance along the threads 42a provided on assembly 90, into the position illustrated in FIG. 49 of the drawings. As assembly 90 advances, penetrating member 84 will penetrate elastomeric member, or pierceable septum 146 and closure wall 136a of the collapsible container 134. Advance of assembly 90 will also cause tubular portion 116b of front housing assembly 116 to telescope forwardly of extension 90a of assembly 90 in the manner shown in FIG. 48 of the drawings.

Relative rotation of housings 42 and 44 will also cause the locking tabs 59 formed on rear plunger housing 58 and a front plunger housing 60 to disengage, thereby permitting spring 62 to urge the front plunger housing 60 to move forwardly of housing 44. As the front plunger housing moves forwardly, the collapsible container will collapse in the manner illustrated in FIG. 49 of the drawings.

Communication between the fluid reservoir 57 and the internal passageway 84a of the penetrating member 84 having been established by the rearward movement of the fluid and delivery control assembly 90, the fluid contained within the fluid reservoir 144 will be expelled from the reservoir as a result of the forward movement of the front plunger housing 60.

From the internal passageway 84a of penetrating member 84, the fluid will flow toward longitudinally extending fluid passageway 107 and then into inlet port 102 formed in rate control housing 106. Next, the fluid will flow into the inlet 100a of the serpentine micro-channel 100, through the micro channel 100 at a controlled rate, through the outlet 100b of the micro channel, into outlet port 104, into passageway 120 and finally into the administration set 40 for delivery to the patient at a precisely controlled rate depending upon the configuration of the micro-channel 100.

As before, so that the caregiver can continuously monitor the amount of fluid remaining within the fluid reservoir 82, indicator means are provided for indicating the volume of fluid contained within the reservoir.

Having now described the invention in detail in accordance with the requirements of the patent statues, those skilled in

The invention claimed is:

1. An apparatus for dispensing medicaments to a patient comprising:
   (a) a first housing;
   (b) a second housing connected to said first housing for relative movement thereto between a first position and a second position;
   (c) an integrally formed, hermetically sealed collapsible container carried by said second housing, said collapsible container having a pierceable top wall and a reservoir for containing a medicinal fluid;
   (d) a plunger assembly disposed within said second housing and operably associated with said container for controllably collapsing said container, said plunger assembly comprising first and second interconnected plunger housings and a spring carried by said first plunger housing for moving said second plunger housing from a first position to a second position; and
   (e) a delivery and control assembly disposed within said first housing, said delivery and control assembly including:
      (i) a rate control base including a piercing member for piercing said pierceable top wall of said container upon movement of said second housing towards said second position;
      (ii) a rate control cover connected to said rate control base; and
      (iii) a fluid flow rate control assembly carried by said rate control base for controlling the rate of fluid flow from said collapsible container toward the patient.

2. The apparatus as defined in claim 1 in which said collapsible container includes a front portion, a rear portion and a collapsible accordion-like, continuous, uninterrupted side wall that interconnects said front and rear portions, said rear portion of said collapsible container including an inwardly extending ullage defining portion.

3. The apparatus as defined in claim 1 in which said collapsible container includes a front portion, a rear portion and a telescoping portion that interconnects said front and rear portions, said rear portion of said collapsible container including an inwardly extending ullage defining portion.

4. The apparatus as defined in claim 1 in which said rate control assembly comprises a rate control plate having at least one micro-channel formed therein in communication with said piercing member.

5. The apparatus as defined in claim 1 further including a rotatable lock for preventing movement between said first and second assemblies.

6. The apparatus as defined in claim 1 in which said plunger assembly includes mating locking tabs for preventing movement of said second housing from said first position to said second position.

7. The apparatus as defined in claim 1 further including a plurality of circumferentially spaced container guides carried within said second housing for positioning said collapsible container there within.

8. The apparatus as defined in claim 1 in which said second housing includes an indicator window for indicating the volume of fluid contained within said collapsible container.

9. An apparatus for dispensing medicaments to a patient comprising:
   (a) a threaded first housing;
   (b) a second housing connected to said first housing, said first threaded housing being movable relative thereto between a first position and a second position;
   (c) an integrally formed, hermetically sealed collapsible container carried by said second housing, said collapsible container having a front portion, including a pierceable top wall; a rear portion; and a side wall that interconnects said front and rear portions, said rear portion of said collapsible container including an inwardly extending ullage defining portion;
   (d) a plunger assembly disposed within said second housing and operably associated with said container for controllably collapsing said container, said plunger assembly comprising:
      (i) a first plunger housing having a plurality of circumferentially spaced locking tabs;
      (ii) a second plunger housing releasably interconnected with said first plunger housing, said second plunger housing having a plurality of circumferentially spaced locking tabs engageable with said plurality of circumferentially spaced locking tabs of said first plunger housing;
      (iii) a spring carried by said first plunger housing for moving said second plunger housing relative to said first plunger housing from a first position to a second position; and
   (e) a delivery and control assembly disposed within said first housing, said delivery and control assembly including:
      (i) a threaded rate control base having a cavity and including a piercing member for piercing said pierceable top wall of said container upon movement of said second housing towards said second position, said piercing member having a fluid passageway;
      (ii) a threaded rate control cover connected to said threaded rate control base; and
      (iii) a fluid flow rate control assembly carried by said rate control base for controlling the rate of fluid flow from said collapsible container toward the patient, said rate control assembly comprising a rate control plate disposed within said cavity of said threaded rate control base, said rate control plate having a micro-channel formed therein, said micro-channel having an outlet and an inlet in communication with said fluid passageway of said piercing member.

10. The apparatus as defined in claim 9 further including a rotatable lock for preventing movement between said first and second assemblies.

11. The apparatus as defined in claim 9 further including an administration line connected to said first housing and being in communication with said outlet of said micro-channel.

12. The apparatus as defined in claim 9 in which said side wall of said collapsible container is accordion-like.

13. The apparatus as defined in claim 9 in which said side wall of said collapsible container comprises a plurality of telescoping portions.

14. The apparatus as defined in claim 9 further including a pierceable septum disposed over said pierceable top wall of said collapsible container.

15. The apparatus as defined in claim 9 in which said second housing includes an indicator window for indicating the volume of fluid contained within said collapsible container.

16. The apparatus as defined in claim 9 further including a plurality of circumferentially spaced container guides carried within said second housing for positioning said collapsible container there within.

17. An apparatus for dispensing medicaments to a patient comprising:
(a) a threaded first housing;
(b) a second housing connected to said first housing, said first threaded housing being movable relative thereto between a first position and a second position, said second housing having an indicator window;
(c) an integrally formed, hermetically sealed collapsible container carried by said second housing, said collapsible container having a front portion, including a pierceable top wall; a rear portion; and a side wall that interconnects said front and rear portions, said rear portion of said collapsible container including an inwardly extending ullage defining portion;
(d) a pierceable septum disposed over said pierceable top wall of said collapsible container;
(e) a plunger assembly disposed within said second housing and operably associated with said container for controllably collapsing said container, said plunger assembly comprising:
(i) a first plunger housing having a plurality of circumferentially spaced locking tabs;
(ii) a second plunger housing releasably interconnected with said first plunger housing, said second plunger housing having a plurality of circumferentially spaced locking tabs engagable with said plurality of circumferentially spaced locking tabs of said first plunger housing; and
(iii) a spring carried by said first plunger housing for moving said second plunger housing relative to said first plunger housing from a first position to a second position;
(f) a delivery and control assembly disposed within said first housing, said delivery and control assembly including:
(i) a threaded rate control base having a cavity and including a piercing member for piercing said pierceable top wall of said container and said pierceable septum upon movement of said second housing towards said second position, said piercing member having a fluid passageway;
(ii) a threaded rate control cover connected to said threaded rate control base; and
(iii) a fluid flow rate control assembly carried by said rate control base for controlling the rate of fluid flow from said collapsible container toward the patient, said rate control assembly comprising:
a. a rate control plate disposed within said cavity of said threaded rate control base, said rate control plate having a serpentine micro-channel etched therein; and
b. a cover plate connected to said rate control plate and cooperating with said serpentine micro-channel to define a fluid passageway in communication with said fluid passageway of said piercing member; and
(g) an administration line connected to said first housing, said administration line being in communication with said outlet of said micro-channel.

18. The apparatus as defined in claim 17 further including a rotatable lock for preventing movement between said first and second assemblies.

19. The apparatus as defined in claim 17 in which said side wall of said collapsible container is accordion-like.

20. The apparatus as defined in claim 17 in which said side wall of said collapsible container comprises a plurality of telescoping portions.

\* \* \* \* \*